US00PP34713P3

(12) United States Plant Patent
Nishikawa

(10) Patent No.: US PP34,713 P3
(45) Date of Patent: Nov. 1, 2022

(54) ***DELOSPERMA* PLANT NAMED 'W1811'**

(50) Latin Name: *Delosperma nubigenum*
Varietal Denomination: W1811

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 0 days.

(21) Appl. No.: 17/557,978

(22) Filed: Dec. 21, 2021

(65) Prior Publication Data

US 2022/0217887 P1 Jul. 7, 2022

(30) Foreign Application Priority Data

Jan. 6, 2021 (QZ) ..... PBR 20211410

(51) Int. Cl.
*A01H 5/02* (2018.01)
*A01H 6/00* (2018.01)
*A01H 6/14* (2018.01)

(52) U.S. Cl.
USPC ..... Plt./422
CPC ..... *A01H 6/00* (2018.05); *A01H 6/14* (2018.05)

(58) Field of Classification Search
USPC ..... Plt./422
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Delosperma* plant named 'W1811' that is characterized by its low growing plant habit, its very floriferous and long blooming flowering habit; blooming from early summer to early autumn, and its flowers that are vivid dark red in color with small yellow centers.

2 Drawing Sheets

Botanical classification: *Delosperma nubigenum.*
Variety denomination: 'W1811'.

CROSS-REFERENCE TO A RELATED APPLICATIONS

This application claims priority to European Community Plant Variety Office (CPVO) Plant Breeder's Rights Application No. 2021/1410 filed on Jun. 1, 2021, under 35 U.S.C. 119(f), the entire contents of which is incorporated by reference herein. This application is also co-pending with a U.S. Plant Patent Application for a plant derived from the same breeding program entitled *Delosperma* Plant Named 'W1813' (U.S. Plant patent application Ser. No. 17/558,045).

BACKGROUND OF THE INVENTION

The present invention relates to a new and distinct cultivar of *Delosperma* plant, botanically known as *Delosperma nubigenum* 'W1811' and will be referred to hereinafter by its cultivar name, 'W1811'. The new cultivar of *Delosperma* is an evergreen perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with a unique range of flower colors.

'W1811' was selected in the Inventor's trial garden in May of 2018 as a single unique plant from amongst the seedlings derived from crosses between unnamed and unpatented plants from the Inventor's breeding program. Seeds were pooled from the crosses and therefore the exact parentage is unknown.

Asexual propagation of the new cultivar was first accomplished by stem cuttings in September of 2018 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'W1811' as a unique cultivar of *Delosperma.*

1. 'W1811' exhibits a low growing plant habit.
2. 'W1811' exhibits a very floriferous and long blooming flowering habit; blooming from early summer to early autumn.
3. 'W1811' exhibits flowers that are vivid dark red in color with small yellow centers.

'W1811' can be most closely compared to the *Delosperma* cultivars 'WOWDAY2' (U.S. Plant Pat. No. 25,645) and 'W1813'. Both are similar to 'W1811' in having low growing plant habits and floriferous and long blooming habits. 'WOWDAY2' differs from 'W1811' in having flowers that are slightly smaller in size and orange-red in color with larger yellow centers and in producing less flowers. 'W1813' differs from 'W1811' in having flowers that are bright orange-red in color with small yellow centers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Concept Plants and Plantipp (both are the breeder's representative for licensing), Globeplanter, and YouTube.

BRIEF DESCRIPTION OF THE DRAWINGS

The accompanying color photographs illustrate the overall appearance and distinct characteristics of the new *Delosperma*. The plant in the photographs is 6 months in age as grown in a 9-cm container in an unheated greenhouse in Noordwijkerhout, The Netherlands.

The photograph in FIG. 1 provides a top view of 'W1811' in bloom.

Figure 1:
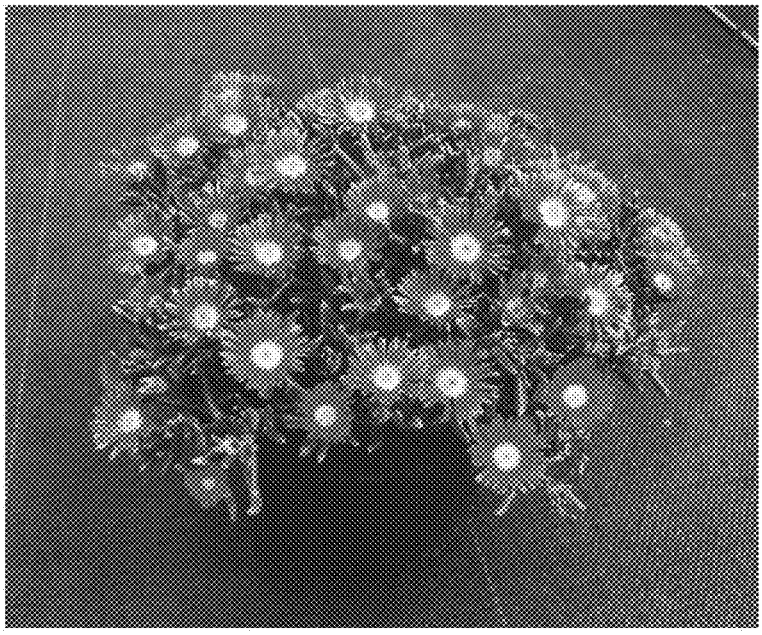
Figure 2:
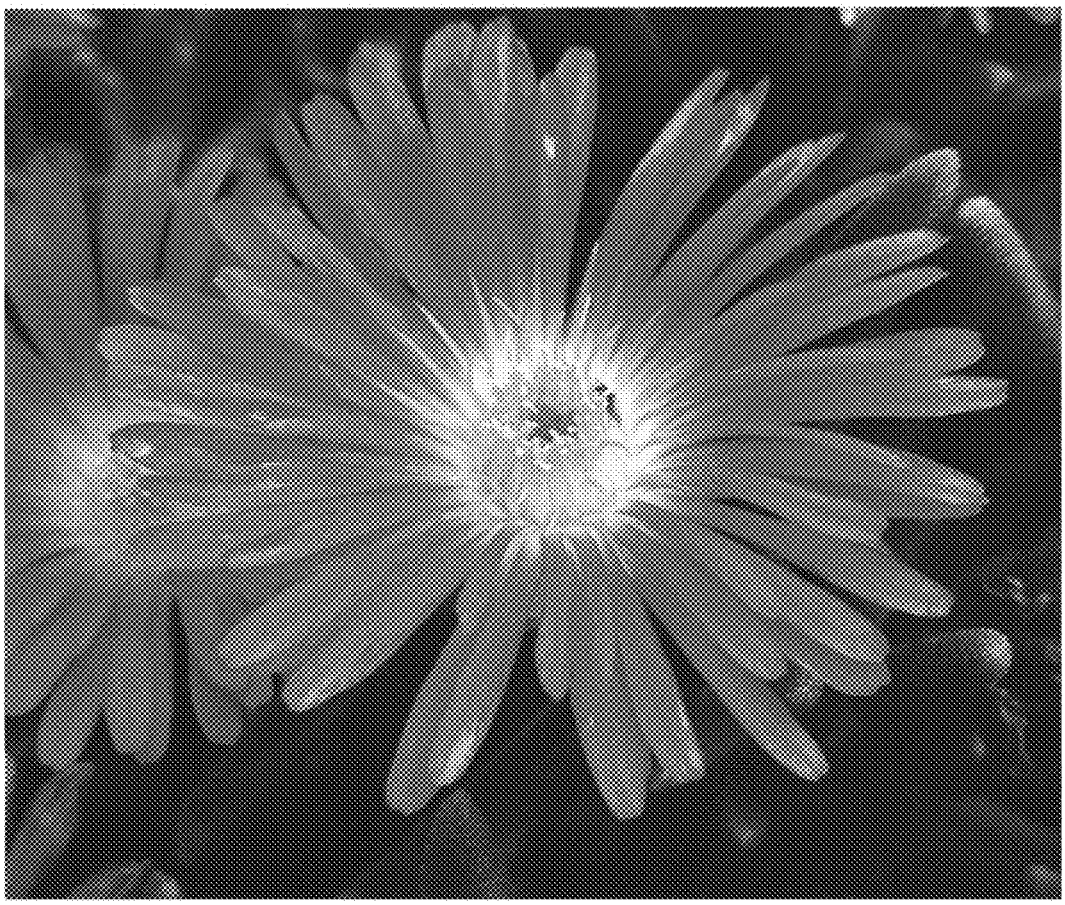

The photograph in FIG. 2 provides a close-up view of a flower of 'W1811'.

The colors in the photograph may differ slightly from the color values cited in the detailed botanical description, which accurately describe the colors of the new *Delosperma*.

DETAILED BOTANICAL DESCRIPTION

The following is a detailed description of 6 months-old plants of the new cultivar as grown in 9-cm containers in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with the 2015; reprint 2019 Colour Chart of The Royal Horticultural Society, London, England, except where general color terms of ordinary dictionary significance are used.

General description:

*Blooming period.*—Blooms from early summer to early autumn in The Netherlands.

*Plant type.*—Evergreen perennial.

*Plant habit.*—Flattened, prostrate.

*Height and spread.*—Reaches an average of 10 cm in height and about 28 cm in diameter as grown in a 9-cm container and reaches 10 to 15 cm in height and 70 to 80 cm in width in the landscape.

*Cold hardiness.*—Observed to be hardy to at least U.S.D.A. Zone 7.

*Diseases and pests.*—No susceptibility or resistance to diseases or pests has been observed.

*Root description.*—Fibrous roots.

*Propagation.*—Stem cuttings.

*Root development.*—8 weeks for root initiation, 4 months from a plug to young plant in a P9 container.

*Growth habit.*—Moderate.

Stem description:

*Shape.*—Round.

*Stem color.*—Young stems; 145C upper side strongly tinged with 182B, older stems 196C to 196D.

*Stem size.*—Lateral branches; an average of 11 cm in length and 2.5 mm in diameter.

*Internode length.*—An average of 3 mm.

*Stem substance.*—Succulent.

*Stem surface.*—Moderately glossy, moderately pubescent with very short glandular hairs; an average of 0.2 mm in length and closest to 155C in color.

*Branching habit.*—Freely branching both basal and lateral, an average of 14 lateral branches per stem.

Foliage description:

*Leaf shape.*—Ligulate, triangular in diameter.

*Leaf substance* .—Succulent.

*Leaf division.*—Simple.

*Leaf base.*—Cuneate.

*Leaf apex.*—Acute.

*Leaf venation.*—No veins visible.

*Leaf margins.*—Entire.

*Leaf arrangement.*—Opposite.

*Leaf surface* (*Upper and lower surface*).—Slightly glossy, sparsely to moderately pubescent with very short glandular hairs; an average of 0.2 mm in length, 157D in color.

*Leaf color.*—Young upper and lower surface; 138B, mature upper surface 137B and lower surface; 137C.

*Leaf size.*—About 2.5 cm in length and 3.5 mm in width.

*Leaf quantity.*—Average of 12 (6 pairs) per lateral branch.

*Leaf attachment.*—Sessile.

Inflorescence description:

*Inflorescence type.*—Flowers solitary, terminal.

*Flower number.*—An average of 1 per lateral stem, per plant; 59 open flowers, 27 flower buds.

*Flower fragrance.*—Faint, sweet and pleasant.

*Flower aspect.*—Outward to upright.

*Flower longevity.*—A few days, self-cleaning.

*Flower type.*—Single.

*Flower size.*—Average of 3.3 cm in diameter and 1.3 cm in depth.

*Flower buds.*—Broadly ovate to oblong in shape, an average of 1 cm in length and 5 mm in diameter, color; 138A with sepal portion 145B.

*Calyx.*—Rotate in shape, average of 5 mm in depth and 1.5 cm in diameter.

*Sepals.*—5, rotate, ovate in shape, margin entire, an average of 7 mm in length and 3 mm in width, broadly acute apex, broadly cuneate base, surface is smooth and dull, color young upper and lower surface; 138A, base 145B, color mature upper and lower surface; 143B to 143C.

*Petals.*—An average of 48 per flower, rotate and slightly curved downward, narrowly flowers that are vivid dark red in color with small yellow centers oblanceolate in shape, surface is smooth and glossy on both surfaces, margin entire, apex obtuse, base cuneate, an average of 1.5 cm in length and 1.5 mm in width, color; opening and fully open flowers upper surface; N45A, center 14B, base NN155C, opening and fully open flowers lower surface; 64B, center and base NN155C.

*Petaloids.*—An average of 30 per flower, rotate and near vertical surrounding stamens, lanceolate in shape, moderately to highly glossy on both surfaces, margin entire, apex obtuse, base truncate, an average of 5 mm in length and 0.75 mm in width, color immature and mature upper and lower surface; NN155C, center to top 14B and N45A.

*Peduncle.*—Average of 1.5 cm in length and 2 mm in diameter, straight on top of lateral branch at 0°, color; a blend between 144B and 145C, surface moderately glossy, sparsely to moderately pubescent with very short glandular hairs.

*Pedicel.*—None.

Reproductive organs:

*Pistils.*—5, an average of 2 mm in length, stigma; triangular shaped, style and stigma; (not distinguishable) combined an average of 2 mm in length and 151B in color, ovary; 143C in color.

*Stamens.*—Average of 60, 12A in color, anthers; dorsifixed and narrowly oblong in shape, an average of 0.5 mm in diameter, filaments; 4 mm in length, NN155D in color, anthers; NN155D in color, pollen; moderate to high in quantity and 6A in color.

*Fruit.*—Fruit and seed production was not observed under the conditions tested.

It is claimed:

1. A new and distinct variety of *Delosperma* plant named 'W1811' as described and illustrated herein.

* * * * *